United States Patent
Ostrer et al.

(10) Patent No.: US 11,650,206 B2
(45) Date of Patent: *May 16, 2023

(54) METHODS AND COMPOSITIONS FOR ASSESSING GERMLINE RISK OF CANCER

(71) Applicant: ALBERT EINSTEIN COLLEGE OF MEDICINE, INC., Bronx, NY (US)

(72) Inventors: Harry Ostrer, New York, NY (US); Johnny C. Loke, Nanuet, NY (US); Alexander Pearlman, New York, NY (US)

(73) Assignee: Albert Einstein College of Medicine, Bronx, NY (US)

(*) Notice: Subject to any disclaimer, the term of this patent is extended or adjusted under 35 U.S.C. 154(b) by 64 days.

This patent is subject to a terminal disclaimer.

(21) Appl. No.: 16/900,194

(22) Filed: Jun. 12, 2020

(65) Prior Publication Data

US 2020/0309781 A1    Oct. 1, 2020

Related U.S. Application Data

(63) Continuation of application No. 15/504,726, filed as application No. PCT/US2015/045856 on Aug. 19, 2015, now Pat. No. 10,718,774.

(60) Provisional application No. 62/039,691, filed on Aug. 20, 2014.

(51) Int. Cl.
    *G01N 33/574* (2006.01)
    *C12Q 1/6886* (2018.01)

(52) U.S. Cl.
    CPC ..... *G01N 33/57496* (2013.01); *C12Q 1/6886* (2013.01); *G01N 33/57415* (2013.01); *G01N 33/57449* (2013.01); *G01N 33/57484* (2013.01); *C12Q 2600/156* (2013.01); *G01N 2333/4703* (2013.01); *G01N 2333/4748* (2013.01); *G01N 2333/9108* (2013.01); *G01N 2440/14* (2013.01); *G01N 2800/50* (2013.01)

(58) Field of Classification Search
    CPC ....... G01N 33/57496; G01N 33/57415; G01N 33/57449; G01N 33/57484; G01N 2333/4703; G01N 2333/4748; G01N 2333/9108; G01N 2440/14; G01N 2800/50; C12Q 1/6886; C12Q 2600/156
    See application file for complete search history.

(56) References Cited

U.S. PATENT DOCUMENTS

| 10,718,774 B2 | 7/2020 | Ostrer et al. |
| 2014/0017678 A1 | 1/2014 | Cesano et al. |
| 2014/0194315 A1 | 7/2014 | Loke et al. |

FOREIGN PATENT DOCUMENTS

| EP | 3183360 B1 | 7/2019 |
| WO | 2016028870 A1 | 2/2016 |

OTHER PUBLICATIONS

Chinese Office Action dated Feb. 23, 2021 received in Chinese Patent Application No. 201580050654.8, together with an English-language translation.
Chinese Office Action dated May 29, 2020 in Chinese Patent Application No. 201580050654.8, together with an English-language translation.
Bogdanova N. et al., "Nigmegen Breakage Syndrome Mutations and Risk of Breast Cancer", Int. J. Cancer 122:802-806 (2008).
Bouwman P. et al., "A High-Throughput Functional Complementation Assay for Classification of BRCA1 Missense Variants", Cancer Discovery 3:1142-1155 (Oct. 2013).
Carvalho M.A. et al., "Determination of Cancer Risk Associated With Germ Line BRCA1 Missense Variants by Functional Analysis", Cancer Research 67(4):1494-1501 (Feb. 15, 2007).
Carvalho M.A. et al., "Functional Assays for BRCA1 and BRCA2", Int J Biochem Cell Biol. 39(2):298-310 (2007).
Casadei S. et al., "Contribution of Inherited Mutations in the BRCA2-Interacting Protein PALB2 to Familial Breast Cancer", Cancer Research 71(6):2222-2229 (Mar. 15, 2011).
Castilla L.H. et al., "Mutations in the BRCA1 Gene in Families With Early-Onset Breast and Ovarian Cancer", Nature Genetics 8:387-391 (Dec. 1994).
Chang S. et al., "Tumor Suppressor BRCA1 Epigenetically Controls Oncogenic MicroRNA-155", Nature Medicine 17(10):1275-1282 (Oct. 2011).
Chen J. et al., "Stable Interaction Between the Products of the BRCA1 and BRCA2 Tumor Suppressor Genes in Mitotic and Meiotic Cells", Molecular Cell 2:317-328 (Sep. 1998).

(Continued)

*Primary Examiner* — Alana Harris Dent
(74) *Attorney, Agent, or Firm* — Scully, Scott, Murphy & Presser, P.C.

(57) ABSTRACT

Heritable mutations in the BRCA1 and BRCA2 and other genes in the DNA double-strand break (DSB) repair pathway increase risk of breast, ovarian and other cancers. In response to DNA breaks, the proteins encoded by these genes bind to each other and are transported into the nucleus to form nuclear foci and initiate homologous recombination. Flow cytometry-based functional variant analyses (FVAs) were developed to determine whether variants in BRCA1 or other DSB repair genes disrupted the binding of BRCA1 to its protein partners, the phosphorylation of p53 or the transport of the BRCA1 complex to the nucleus in response to DNA damage. Each of these assays distinguished high-risk BRCA1 mutations from low-risk BRCA1 controls. Mutations in other DSB repair pathway genes produced molecular phenocopies with these assays. FVA assays may represent an adjunct to sequencing for categorizing VUS or may represent a stand-alone measure for assessing breast cancer risk.

16 Claims, 9 Drawing Sheets

(9 of 9 Drawing Sheet(s) Filed in Color)

(56) References Cited

OTHER PUBLICATIONS

Desjardins S. et al., "Variations in the NBN/NBSI Gene and the Risk of Breast Cancer in Non-BRCAI/2 French Canadian Families With High Risk of Breast Cancer", BMC Cancer 9:181 (Jun. 2009).

Friedman L.S. et al., "Confirmation of BRCA1 by Analysis of Germline Mutations Linked to Breast and Ovarian Cancer in Ten Families", Nature Genetics 8:399-404 (Dec. 1994).

Gorski B. et al., "Founder Mutations in the BRCA1 Gene in Polish Families With Breast-Ovarian Cancer", Am. J. Hum. Genet. 66:1963-1968 (2000).

Gowen L.C. et al., "Brca1 Deficiency Results in Early Embryonic Lethality Characterized by Neuroepithelial Abnormalities", Nature Genetics 12:191-194 (Feb. 1996).

Hakem R. et al., "The Tumor Suppressor Gene Brca1 is Required for Embryonic Cellular Proliferation in the Mouse", Cell 85:1009-1023 (Jun. 28, 1996).

Heikkinen K. et al., "RAD50 and NBS1 are Breast Cancer Susceptibility Genes Associated With Genomic Instability", Carcinogenesis 27(8):1593-1599 (2006).

Hsu H-M et al., "Breast Cancer Risk is Associated With the Genes Encoding the DNA Double-Strand Break Repair Mre11/Rad50/Nbs1 Complex", Cancer Epidemiol Biomarkers Prev 16(10):2024-2032 (2007).

Jara L. et al., "Molecular Analysis of the Eighteen Most Frequent Mutations in the BRCA1 Gene in 63 Chilean Breast Cancer Families", Biol Res 37:469-481 (2004).

Lee M.S. et al., "Comprehensive Analysis of Missense Variations in the BRCT Domain of BRCA1 by Structural and Functional Assays", Cancer Research 70(12):4880-4890 (Jun. 15, 2010).

Loke J. et al., "Mutations in MAP3K1 Tilt the Balance from SOX9/FGF9 to WNT/B-Catenin Signaling", Human Molecular Genetics 23(4):1073-1083 (2014).

Loke J. et al., "Rapidly Screening Variants of Uncertain Significance in the MAP3K1 Gene for Phenotypic Effects", Clinical Genetics 81:272-277 (2012).

Mannucci A. et al., "Biomass Accumulation Modelling in a Highly Loaded Biotrickling Filter for Hydrogen Sulphide Removal", Chemosphere 88:712-717 (2012).

Murray M.L. et al., "Follow-Up of Carriers of BRCA1 and BRCA2 Variants of Unknown Significance", Variant Reclassification and Surgical Decisions, Genetics in Medicine 13(12):998-1005 (Dec. 2011).

Scully R. et al., "Association of BRCA1 With Rad51 in Mitotic and Meiotic Cells", Cell 88:265-275 (Jan. 24, 1997).

Seal S. et al., "Truncating Mutations in the Fanconi Anemia J Gene BRIP1 are Low-Penetrance Breast Cancer Susceptibility Alleles", Nature Genetics 38(11):1239-1241 (Nov. 2006).

Serova O. et al., "A High Incidence of BRCA1 Mutations in 20 Breast-Ovarian Cancer Families", Am. J. Hum. Genet. 58:42-51 (1996).

Stacey S.N. et al., "The BARD1 Cys557Ser Variant and Breast Cancer Risk in Iceland", PLoS Medicine 3 (7):1103-1113 (Jul. 2006).

Starita L.M. et al., "Substrates of the BRCA1-Dependent Ubiquitin Ligase", Cancer Biology & Therapy 5(2):137-141 (Feb. 2006).

Struewing J.P. et al., "Detection of Eight BRCAI Mutations in 10 Breast/Ovarian Cancer Families, Including I Family With Male Breast Cancer", Am. J. Hum. Genet. 57:1-7 (1995).

Struewing J.P. et al., "The Carrier Frequency of the BRCA1 185delAG Mutation is Approximately 1 Percent in Ashkenazi Jewish Individuals", Nature Genetics 11:198-200 (Oct. 1995).

Tonin P. et al., "Frequency of Recurrent BRCA1 and BRCA2 Mutations in Ashkenazi Jewish Breast Cancer Families", Nature Medicine 2(11):1179-1183 (Nov. 1996).

Venkitaraman A.R., "Cancer Suppression by the Chromosome Custodians, BRCA1 and BRCA2", Science 343:1470-1475 (Mar. 28, 2014).

Venkitaraman A.R., "Linking the Cellular Functions of BRCA Genes to Cancer Pathogenesis and Treatment", Annu. Rev. Pathol. Mech. Dis. 4:461-487 (2009).

Wang Y. et al., "BASC, a Super Complex of BRCA1-Associated Proteins Involved in the Recognition and Repair of Aberrant DNA Structures", Genes and Development 14:927-939 (2000).

International Search Report dated Nov. 24, 2015 issued in PCT/US2015/045856.

Huen et al., "BRCA1 and its toolbox for the maintenance of genome integrity", Nat Rev Mol Cell Biol. (Feb. 2010), vol. 11, No. 2, pp. 138-148.

Becker A.A. et al., "A 24-Color Metaphase-Based Radiation Assay Discriminates Heterozygous BRCA2 Mutation Carriers from Controls by Chromosomal Radiosensitivity", Breast Cancer Res Treat 135:167-175 (2012).

Febrer E. et al., "Mitotic Delay in Lymphocytes from BRCA1 Heterozygotes Unable to Reduce the Radiation-Induced Chromosomal Damage", DNA Repair 7:1907-1911 (2008).

Trenz K. et al., "Mutagen Sensitivity of Peripheral Blood from Women Carrying a BRCA1 or BRCA2 Mutation", Mutation Research 500:89-96 (2002).

Vilasova Z. et al., "Changes in Phosphorylation of Histone H2A.X and p53 in Response of Peripheral Blood Lymphocytes to Gamma Irradiation", Acta Biochimica Polonica 55(2):381-390 (2008).

Extended Supplementary European Search Report dated Feb. 9, 2018 received in European Patent Application No. 15 83 3376.5.

European Office Action dated Nov. 15, 2018 issued in EP 15 833 376.5.

Keimling M. et al., "The power of DNA double-strand break (DSB) repair testing to predict breast cancer susceptibility", The FASEB Journal, (2012), vol. 26, No. 5, pp. 2094-2104.

Syeda M.M. et al., "Prediction of breast cancer risk based on flow-variant analysis of circulating peripheral blood B cells", Genetics in Medicine, (2017), 7 pages doi:10.1038/gim.2016.222.

Examination Search Report dated Jul. 29, 2022 received in CA Application No. 2,958,550, 3 pages.

METHODS AND COMPOSITIONS FOR ASSESSING GERMLINE RISK OF CANCER

CROSS REFERENCE TO RELATED APPLICATION

This application is a continuing application of U.S. Ser. No. 15/504,726 filed Feb. 17, 2017, which claims the benefit of priority from U.S. Provisional Application No. 62/039,691, filed Aug. 20, 2014, the entire contents of which are incorporated herein by reference.

FIELD OF THE DISCLOSURE

This invention relates to methods and compositions for assessing germline risk of cancer (e.g., breast and ovarian cancer) based on analysis in circulating blood cells of cytoplasmic and nuclear proteins in the DNA double stranded breakage (DSB) repair pathway.

BACKGROUND ART

Individuals from high-risk breast cancer families comprise about 10% of incident cases. Among these individuals, germline mutations in the BRCA1 and BRCA2 genes can be detected in 20-40% of cases (TONIN et al., Nature Medicine, 2:1179-1183 (1997)). Other moderate to high penetrance genes contribute to heritable breast cancer predisposition (MANNUCCI et al., Chemosphere, (2012)). These genes tend to share common pathways with BRCA1 and 2 and play a role in the repair of double-stranded breaks in DNA. Homozygous mutations in some of these genes cause Fanconi anemia (FA), ataxia telangiectasia and Nijmegen breakage syndrome. The 14 FA genes work together in concert with BRCA1 in a common DNA repair pathway and, if mutated, convey risk for breast cancer. In response to DNA damage (FIG. 1), ATM (ataxia telangiectasia mutated) and ATR (ataxia telangiectasia and Rad3-related) kinases activate the FA core complex comprising FANCA, B, C, E, F, G, L, and M, which then monoubiquinates FANCD2 and FANC1. This complex then interacts with other downstream proteins, FANCD1 (BRCA2), FANCN (PALB2), and FANCJ (BRIP1) to initiate DNA repair through homologous recombination. BRCA1 has also been identified as an upstream regulator of the PALB2/BRCA2 complex, promoting its localization to DNA damage sites (CASADEI et al., Cancer Res, 71:2222-2229 (2011)). BRCA1 exists mostly as a heterodimer with BARD1 forming a ubiquitin ligase that is instrumental in BRCA1 response to DNA damage (STARITA et al., Cancer Biol Ther 5:137-141 (2006)). PALB2, BRIP1, and BARD1 gene mutations have been associated with increased risk of breast cancer (SEAL et al., Nat Genet 38:1239-1241 (2006); STACEY et al., PLoS Med 3:e217 (2006)).

Nijmegen breakage syndrome is an autosomal recessive chromosome instability syndrome of microcephaly, growth retardation, intellectual disability, immunodeficiency, and increased risk of malignancy, caused by mutations in the NBN gene (BOGDANOVA et al., Int J Cancer, 122:802-806 (2008)). NBN forms a complex with MRE11A and RAD50 to form the Mre11 complex necessary for DNA double stranded break repair (HEIKKINEN et al., Carcinogenesis, 27:1593-1599 (2006); DESJARDINS et al., BMC Cancer, 9:181 (2009)). This complex co-localizes with BRCA1 as well as with FANCD2 in response to DNA damage (WANG et al., Genes Dev, 14:927-939 (2000)). Heterozygous mutations in NBN, MRE11A, or RAD50 have been found to be associated with increased risk of breast cancer (BOGDANOVA et al., Int J Cancer, 122:802-806 (2008); HEIKKINEN et al., Carcinogenesis, 27:1593-1599 (2006); HSU et al., Cancer Epidemiol Biomarkers Prev, 16:2024-2032 (2007)).

Informatics approaches have been taken for curating newly identified genetic variants to determine whether they are pathogenic. These informatics approaches combine prior probabilities of causality derived from an evolutionary sequence conservation model (Align-GVGD) with the likelihood of how the variant segregates with cancer in sequenced families, whether the variant is seen in combination with a known pathogenic mutation (which should be lethal for BRCA1 or cause FA for BRCA2, if the variant is pathogenic), the age of onset and cancer type associated with the variant, and the histology of the associated breast tumors. The accuracy of the Align-GVGD method may be high; however, it requires sequencing for calling variants and may overweigh high-penetrance variants, since moderate penetrance variants would simply not show the co-transmission with the cancer phenotype.

SUMMARY OF THE DISCLOSURE

This invention is directed to methods and compositions for assessing germline risk of cancer (e.g., breast and ovarian cancer) based on analysis in circulating blood cells of proteins in the DNA double stranded breakage (DSB) repair pathway. Mutations in genes within this pathway, BRCA1, BRCA2, FANCD1, NBN and others, may be lethal or cause Fanconi anemia (FA) in the homozygous state and increase risk for breast and ovarian cancer in the heterozygous state. The methods disclosed herein measure functionality of each molecular phenotypes caused by variants in these genes that are indicative of mutational status and, therefore, germline genetic risk. Identification of these variant driven phenotypes can be implemented either as an adjunct to DNA sequencing especially for annotating variants of uncertain significance, or as a standalone method for risk assessment.

The methods of this invention are particularly useful in at least two aspects: (i) the present methods provide functional annotation of variants of uncertain significance (VUS) identified by genetic sequencing; and (ii) the present methods permit evaluation of germline risks not identified by DNA sequencing of BRCA1 and BRCA2. Individuals from high-risk breast cancer families comprise about 10% of incident cases. Among these individuals, germline mutations in the BRCA1 and BRCA2 genes can be detected in 20-40% of cases. In 90-95% of cases, these DNA variants can readily be shown to disrupt gene function, because they are nonsense, small out-of-frame insertion or deletion mutations, larger gene rearrangements, and truncating splicing alterations. In 5-10% of DNA sequencing tests (higher in some countries), VUS are identified. Among the remaining 60-80% of individuals from high-risk families, mutations may be found in other genes in the BRCA1-FA pathway. Annotating variants identified in these genes may present the same difficulties as those confronted when annotating variants in BRCA1 and BRCA2. In an undefined percentage of cases, a mutation cannot be found in a known risk gene.

In addition to categorizing mutations, these novel methods may also represent an alternative to genomic sequencing for identifying functionally important genetic variants. Most sequencing methods are limited in scope and depth—with certain genomic regions being difficult to capture, amplify or assemble. These limitations commonly result in finished sequences that comprise less than the whole of the desired region. Thus, important functional variants may be missed. A direct functional test at protein level bypasses this concern, by querying whether a key biological function is being compromised and, thus, might be more sensitive and specific for identifying genetic risks. Because these assays use standard reagents (commercial antibodies and magnetic beads) and readily available technology (flow cytometry), they lend themselves to ease of adoption in the research and clinical laboratory environments with minimal change of equipment and workflow.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

DETAILED DESCRIPTION

Figure 1:
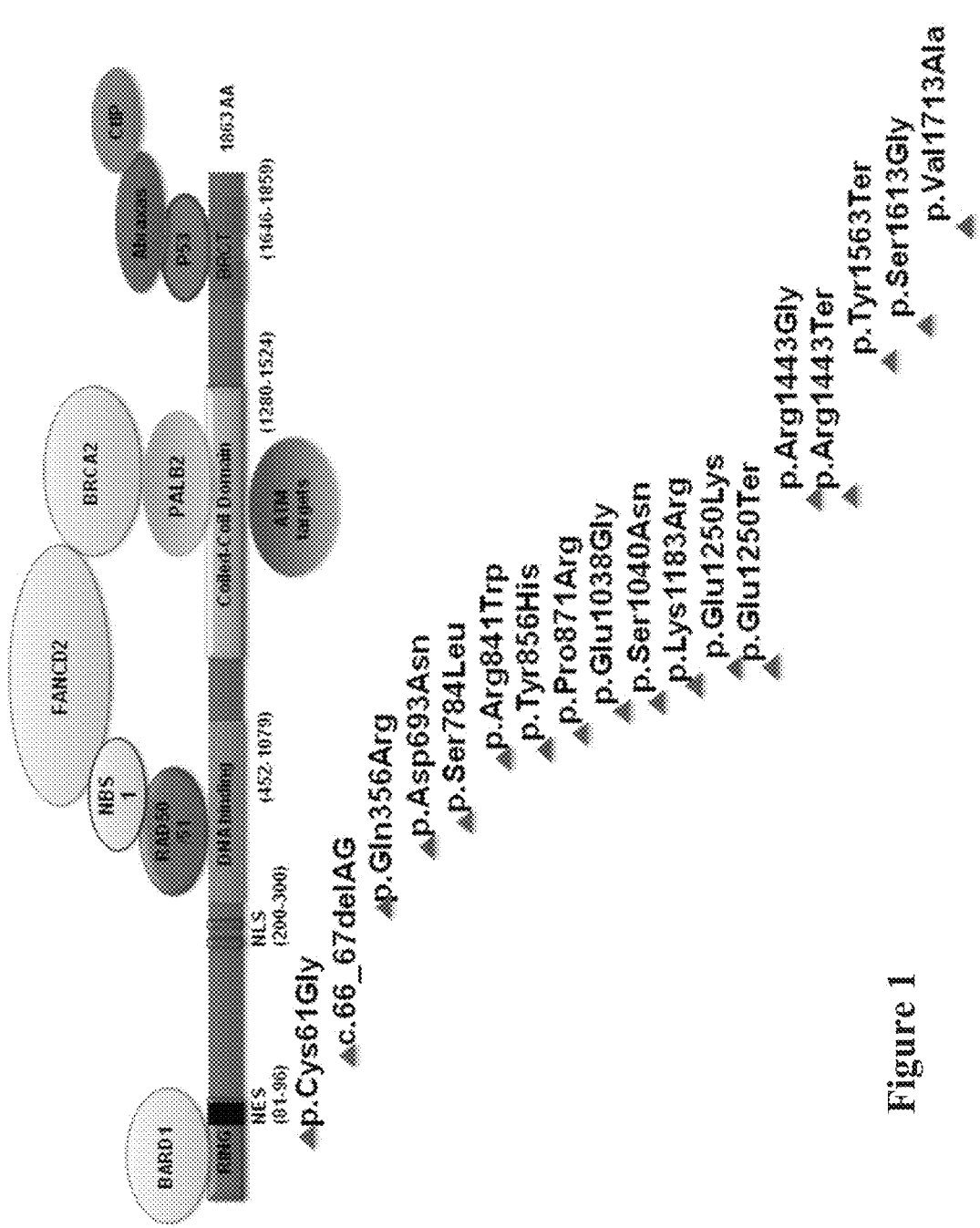
FIG. 1. Map of BRCA1 protein demonstrating binding partners and binding sites. Cell lines included known pathogenic mutations (red), benign wild type variants (blue) and VUS (purple).

The methods disclosed herein for assessing germline risk of breast cancer or ovarian cancer are based on functional variant analysis (FVA) in white blood cells (WBCs) from whole blood of a subject of interest, particularly a human subject.

The phrase "white blood cells", as used herein, includes lymphocytes (i.e. T cells and B cells), monocytes, neutrophils, eosinophils, and basophils. In specific embodiments, B cells are isolated and used in the analysis.

The term "functional variant analysis", as used herein, refers to analysis designed to determine the functional phenotype of variants in a gene of interest, i.e., whether a variant in a gene of interest encodes a protein that is functional, partially functional, or not functional. The functionality of the protein can be evaluated in various assays depending on the biological functions of the protein, and can in many instances be correlated with pathogenicity of a disease (e.g., cancer). A variant in a gene of interest encodes a protein that is functional if it is determined that the functionality of the encoded protein has at least 80%, 85%, 90%, 95% or greater of the functionality of the protein encoded by a wild type gene. Functional variants include gain of function variants, namely, the functionality of the encoded protein is enhanced by at least 10%, 15%, 20%, 25%, 50%, 75% or more as compared to the protein encoded by a wild type gene. A variant in a gene of interest encodes a protein that is partially functional if it is determined that the functionality of the encoded protein has between 20%-80%, e.g., 20%, 30%, 40%, 50%, 60%, 70% or 80% of the functionality of the protein encoded by a wild type gene. A variant in a gene of interest encodes a protein that is not functional if it is determined that the functionality of the encoded protein has less than 20%, 15%, 10%, 5% or less of the functionality of the protein encoded by a wild type gene.

In some embodiments, the functional variant analysis is designed to evaluate the functionality of variants of genes in the DNA double-strand break (DSB) repair pathway. Such genes include ATM, BRCA1, BRCA2, PALB2, FANG gene group (e.g., FANCD2, FANCC, FANCF), NBN, BARD1, p53, RAD50/51, NBS1, Abraxas, CtIP, and DNA Ligase genes for example.

In specific embodiments, the functional variant analysis is designed to evaluate whether variants in BRCA1 or other DSB repair genes show disrupted or reduced binding of BRCA1 to its protein partners (e.g., PALB2, BRCA2, or FANCD2), disrupted or reduced phosphorylation of p53, and/or disrupted or reduced transport of the BRCA1 complex to the nucleus, in response to DNA damage.

In accordance with this disclosure, a DNA damaging agent is applied to the cells (i.e., white blood cells) to permit manifestation and evaluation of the functionality of variants in BRCA1 or other DSB repair genes. DNA damaging agents suitable for use in this invention includes all agents that cause DNA double strand breaks or DNA cross-linking, including radiation, such as UV (200-400 nm) and radiation at other frequencies (e.g., x-ray, gamma rays); thermal disruption; chemical compounds such as known mutagens (e.g., MMC, DEB, Bleo), and combinations thereof.

The cells treated with a DNA damaging agent are then analyzed in one or more functional variant analysis (FVA) assays. The results are then compared to control values, e.g., values from cells having a variant known to be associated with breast cancer and/or ovarian cancer, and/or normal type cells having a gene sequence known not to be associated with breast cancer or ovarian cancer. The control values can be provided based on evaluation at an earlier time, or can be obtained based on evaluation performed side-by side with testing cells.

In accordance with this disclosure, one or more FVA assays can be performed to determine the functionality of the variants in BRCA1 gene and/or other DSB genes, thereby determining the risk of the subject having or developing breast and/or ovarian cancer. In some embodiments, one FVA assay is performed and selected from a BRCA1 nuclear localization assay, a binding assay (binding of partners, such as PALB2, BRCA2, or FANCD2 to BRCA1), or a p53 phosphorylation assay. In specific embodiments, the FVA assay is a BRCA1 nuclear localization assay. In other embodiments, at least two FVA assays are performed. In some embodiments, the two FVA assays are selected from those pairs in Table 2 having an "r" value of at least 0.82. In other embodiments, the two FVA assays are selected from those pairs in Table 2 having an "r" value of at least 0.84. In still other embodiments, two FVA assays are selected from those pairs in Table 2 having an "r" value of at least 0.91. In specific embodiments, the two FVA assays are selected from the combination of p53 phosphorylation assay and BRCA1 nuclear localization assay in response to MMC, or the combination of BRCA1 nuclear localization assay in response to DEB and BRCA1 nuclear localization assay in response to a cocktail of MMC, DEB and Bleo. Performance of multiple FVA assays provides a more accurate determination of whether the variants present in the subject are pathogenic (i.e., associated with cancer) or not.

For each type of FVA assays, one can utilize any of the conventional assay formats. For example, to evaluate BRCA1 nuclear localization, conventional Western Blot analysis, ELISA and any other suitable protein assays, can be used. In specific embodiments, digital cell Western (DCW-NUCLEAR LOCALIZATION) is used as illustrated in the examples, which requires much fewer starting cells and is faster and more sensitive. Similarly, to evaluate protein binding to BRCA1, conventional immunoprecipitation can be utilized. In specific embodiments, a high throughput format utilizing magnetic beads, differential gating and flow cytometry is employed. To evaluate p53 phosphorylation, convention methodologies for assaying phosphorylation of p53 can be used, although in specific embodiments, digital cell Western (DCW-NUCLEAR LOCALIZATION) is used as illustrated in the examples.

Based on the results of the FVA analysis, it can be determined whether the variants in the BRCA1 gene or other DSB repair genes are likely associated with breast and/or ovarian cancer. It should be noted that the present methods determine the likelihood or risk, without necessarily predicting with certainty or sequence results. For example, when the FVA assay is a BRCA1 nuclear localization assay, a substantial reduction of BRCA1 nuclear localization in cells being tested as compared to normal cells indicates likelihood that the BRCA1 variant in the subject is a variant associated with cancer.

The present description is further illustrated by the following examples, which should not be construed as limiting in any way. The contents of all cited references (including literature references, issued patents, and published patent applications as cited throughout this application) are hereby expressly incorporated by reference.

Example 1. Digital Cell Western and Nuclear Localization Assay

This Example describes exemplary protocols and reagents used for digital cell Western and nuclear localization assay.

A. Fix Cells—Adherent Cells Protocol:
1. Trypsinize adherent cells prior to fixation and collect the culture in a 50 ml Falcon tubes.
2. Vortex, count cells (20 uL Trypan Blue+20 ul cell culture in a tube, then put 10 ul of the mix on Countess cell counting chamber slide) and record.
3. Centrifuge to remove media-trypsin mix and resuspend the cells with 500 ul culture media. If there is a larger pellet, add more media.
4. Mix the cells by pipetting to avoid any clumping before fixation or it will fix aggregated cells as one.
5. Add ⅕th or 100 ul of 'Inhibitor Mix Cocktail' in to the cells.
6. Mix by vortex briefly and incubate at 37° C. with 5% $CO_2$ for 10 minutes.
7. If a larger volume of fixation media is used, centrifuge the cells to pellet and remove all media from the falcon tube.
8. Add 1-25 ml of ice-cold methanol depending of desired cell density, vortex and place on ice for 5 minutes or more.
9. Cells can be transferred to storage tubes or plates, which should be tight to avoid methanol evaporation.
10. Cells can be stored in −80° C. for up to 2 years. Or a week at 4° C. Shipment of cells should be on dry ice or cold pack if the shipment distance is less than a week.

B. Conjugate Fluorophore to Antibody:
Use Novus Biologicals Kit: Lightning Link R-Phycoerythrin Conjugation Kit Protocol #703-0010.
1. Add 1 ul of LL-Modifier reagent (10× stock) for each 10 ul of antibody to be labeled (10 ul total). Mix gently.
2. Remove the screw cap from the vial of Lightning-Link-Antibody mix and pipette the mix directly into the lyophilised material in the vial. Resuspend gently by withdrawing and re-dispensing the liquid once or twice using a pipette, incubate overnight at room temperature in drawer (dark).
3. Store at −20° C.

C. Conjugate Antibody/Fluorophore onto Beads:
Dynabeads® Co-Immunoprecipitation Kit—Catalog number 14321D.

Antibody Coupling Protocol (Step #3)—If not already done so, resuspend beads in Storage Buffer at 10 mg/mL; use 1 mL of beads. Use 5 μg of antibody per 1 mg of beads=50 μg antibody total.

Day 1:
1. Disinfect the magnet to prevent accidental sample contamination.
2. Pipette the appropriate amount of Dynabeads® M-270 Epoxy (see Calculation of Antibody and C1 Volumes in the following table).
3. Wash the beads with 1 mL of C1 and mix by vortexing or pipetting.
4. Place the tube on a magnet for 1 min and allow the beads to collect at the tube wall. Remove the supernatant.
5. Add the appropriate volume of antibody+C1 (see Calculation of Antibody and C1 Volumes in the following table) to the washed beads and mix by gentle vortexing or pipetting.
   Example: If you are coupling 5 mg Dynabeads®M-270 Epoxy and your required quantity of antibody has a volume of 100 µL, you should add 150 µL of C1 (i.e., 250 µL C1-100 µL Ab=150 µL).
6. Add the appropriate volume of C2 and mix by gentle vortexing or pipetting.
   Calculation of Antibody and C1 Volumes
   Generally speaking, The C1+Ab volume is equal to C2 volume. The total reaction volume (C1+µL Ab+C2) should be 100 µL per mg beads.
7. Incubate on a roller at 37° C. overnight (16-24 hours). The fluid in the tube should be mixing well.

Day 2
1. Place the tube on a magnet for 1 min and allow the beads to collect at the tube wall. Remove the supernatant.
2. HB wash: Add the appropriate volume of HB and mix by vortexing or pipetting. Beads (mg) Volume HB (µL) 10 mg beads=800 ul HB
3. Place the tube on a magnet for 1 min and allow the beads to collect at the tube wall. Remove the supernatant.
4. LB wash: Add the appropriate volume of LB and mix by vortexing or pipetting. 10 mg beads=800 ul LB
5. Place the tube on a magnet for 1 min and allow the beads to collect at the tube wall. Remove the supernatant.
6. Short SB wash: Add the appropriate volume of SB and mix by vortexing or pipetting. 10 mg beads=800 ul LB
7. Place the tube on a magnet for 1 min and allow the beads to collect at the tube wall. Remove the supernatant.
8. Repeat Short SB wash once more.
9. Long SB Wash: Add the appropriate volume of SB and mix by vortexing or pipetting. 10 mg beads=800 ul LB
10. Incubate on a roller/rotator at room temperature for 15 min.
11. Place the tube on a magnet for 1 min and allow the beads to collect at the tube wall. Remove the supernatant.
12. Resuspend antibody-coupled beads in 100 µL SB per mg beads and store at 2° C. to 8° C. until use.
    10 mg beads=1 mL SB buffer
The final bead concentration is 10 mg/mL antibody-coupled beads.

D. Combine Cells with Antibody/Fluorphore/Bead Complex:
1. Use 200,000 ($2 \times 10^5$) fixed cells in methanol per well on a 96 well plate.
2. Spin at 5,000 g for 5 minutes to pellet cells.
3. Remove methanol by flicking and drying.
4. Wash with 200 µl of Universal FVA buffer—Spin at 5,000 g for 5 minutes to pellet cells. Remove supernatant by flicking and drying.
5. Repeat Step #4.
6. Resuspend cells in 20 µl of Universal FVA buffer.
7. Determine how much antibody is needed for the experiment—Add 1 µl of LL-quencher (10× stock) reagent for every 10 µl of antibody used.
8. Add antibody to the 20 µl of cells in 96 wp at desired concentration (1:20 dilution is default).
9. Incubate for 30 minutes on ice (on shaker is recommended when available).
10. To wash, add 200 µl of Universal FVA buffer directly into the 96 wp and spin at 5,000 g for 5 minutes to pellet cells, flick to remove supernatant, repeat the wash once again.
11. Resuspend in 180 µl of Universal FVA buffer and place the plate on ice until the run.
12. Run on flow machine (takes 30 minutes to setup the machine so get there early).

Conjugated cells/antibodies is good for 10 hrs. Signal decay starts at 2 hrs.

DCW-NUCLEAR LOCALIZATION Assay Short Protocol:

As an example, for the BRCA1 FVA nuclear localization assays, the cultured cells were serum-starved for 24 hours prior to treatment either by the vehicle or the radiomimetic drugs: 0.1 µg/ml Bleomycin, 0.5 µg/ml 1,3-butadiene diepoxide (DEB), and/or 1.5 µg/ml Mitomycin C (MMC), or combination thereof, for 24 hours.

For nuclear extraction of cells, 200,000 cells were washed with PBS, then lysed using Cytolysis Buffer (e.g. Active Motive 10× hypotonic buffer, Cat. 40010). This results in cytolysis of about at least 50% of cells. The prep was then spun, and the pellet containing nuclei and unlysed cells was resuspended in Universal FVA buffer (50 mM Sodium Tris-HCl pH 7.4, 0.02% sodium azide). The whole prep was probed with fluorochrome-conjugated anti-BRCA1 and an antibody to a cytoplasmic marker (e.g., an endoplasmic reticulum detection antibody) which distinguishes intact cells from nuclei population. Samples were also stained with DAPI and flow sorted and prior to quantification.

Adjusting for size and complexity using Forward Scatter (FSC) and Side Scatter (SSC) parameters on the flow cytometer to capture heterogeneous population of beads (at least 5-fold difference), setting should be set to log scale for both FSC and SSC to low setting. Then a stopping gate is defined to a population of interest for the samples, to at least 50,000 events.

The binding of endogenous mutant BRCA1-interacting proteins was measured by the FVA co-immunoprecipitation bead assays on Dynal magnetic beads. Using BRCA1 as bait, the binding of partners, not limited, such as BRCA2, PALB2, BARD1, and FANCD2 were gated and quantified using fluorchrome-conjugated primary antibodies. The binding of the protein complexes were compared for among the mutants, VUS and wild type LCLs.

Reagents
Paraformaldehyde (20×) or Formaldehyde Solution
1. Add 10 g of EM grade paraformaldehyde to 25 ml of 1×PBS.
2. Add 1 ml of NaOH (~4 pellets) and stir gently on a heating block at ~60° C. until the PFA is dissolved. Allow the mixture to cool at room temperature.
3. Adjust the pH to 7.4 with 1M HCl then adjust the final volume to 50 ml by adding 25 ml of PBS.
4. Filter the solution through a 0.45 um (or less) membrane filter to remove any particular matter.
5. Store in aliquots a ~20° C. for several months. Avoid light sources and repeated freeze/thawing.

Formaldehyde Solution: Sigma #F8775-25 mL.
Inhibitor-Fixation Mix Cocktail (10×)
Roche 'Complete phosStop tabs' 04906845001 (follow manufacturer recommendations), e.g. 2 tab in 10 ml of buffer.
Roche 'Complete mini-EDTA free tabs' 04693159001 (follow manufacturer recommendations), e.g., 1 tab in 10 ml of buffer.
20% Formaldehyde (PFA) prepared freshly and add to the inhibitors prior to treatment. For example, 10 ml of PFA with 2 tablets of PhosphoStop and 1 tablet of Complete Protease Inhibitor.

Permealizing Agent
100% ice-cold Methanol
Cytolysis Buffer
Active Motive 10× hypotonic buffer, Cat. 40010, mix 50 ml of the buffer in 450 ml of water.

Universal FVA Buffer (Good for 6 Months at 4° C.)
50 mM Sodium Tris-HCl ph 7.4
0.02% Sodium Azide
Lightning Link R-Phycoerythrin Conjugation Kit—#703-0010
Dynabeads® Co-Immunoprecipitation Kit—14321D
Other:
0.25% Trypsin
PBS
2× Trypan Blue Example 2

This Example describes three different types of analyses performed to evaluate the effects of different genetic variants: 1. protein co-immunoprecipitation to assess co-factor binding to BRCA1, 2. digital cell Western to assess total and phospho-p53, and 3. nuclear localization in the presence or absence of DNA clastogenic or cross-linking agents.

The present invention is not limited to the above specific examples. Another exemplary protocol contemplated by the present invention is characterized by recovering magnetic beads complexes from the sample by applying a magnetic field; recovering non-magnetic bead complexes from the sample based on a non-magnetic physical property of the non-magnetic beads; passing the recovered magnetic bead complexes through a flow cytometer or optical plate reader; passing the recovered non-magnetic bead complexes through a flow cytometer or optical plate reader; detecting the optical signal(s) of the recovered magnetic bead complexes; and detecting the optical signal(s) of the recovered non-magnetic bead complexes; wherein the presence on a magnetic bead complex of only a secondary optically-active label indicates the interaction between the first protein A and a second protein corresponding to the secondary optically-active labeled secondary agent.

The kit contemplated by the present invention may include, but not be limited to the following components polystyrene-epoxy paramagnetic (Dynabeads) beads (5 µM) in storage buffer, carboxylate-modified polystyrene surface latex (CML) beads (5 µm) in storage buffer, 10 ml of Flow grade neutral buffered salt solution, pH 7.4. Examples of additional contemplated buffers useful in accordance with the invention include Phosphate Buffered Saline, Phosphate Buffeted KCL, Trisaminomethane (Tris)-buffered ammonium chloride and the like.

Results

Annotation of BRCA1 Variant-Bearing Cell Lines.

Figure 6:
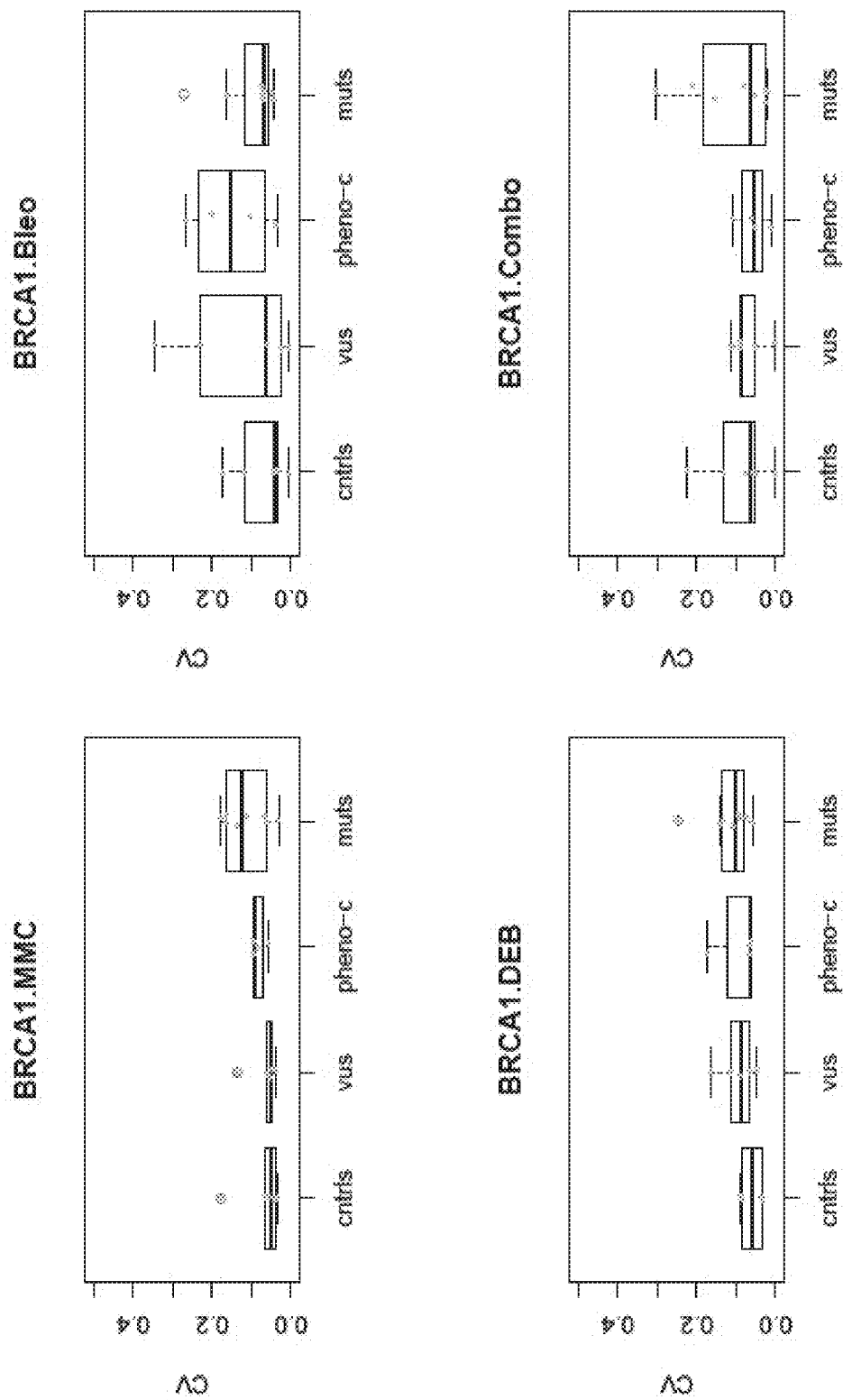
FIG. 6. Nuclear localization assays have small coefficients of variation (CVs). Boxplots of CVs of individual nuclear localization assays.
Figure 7:
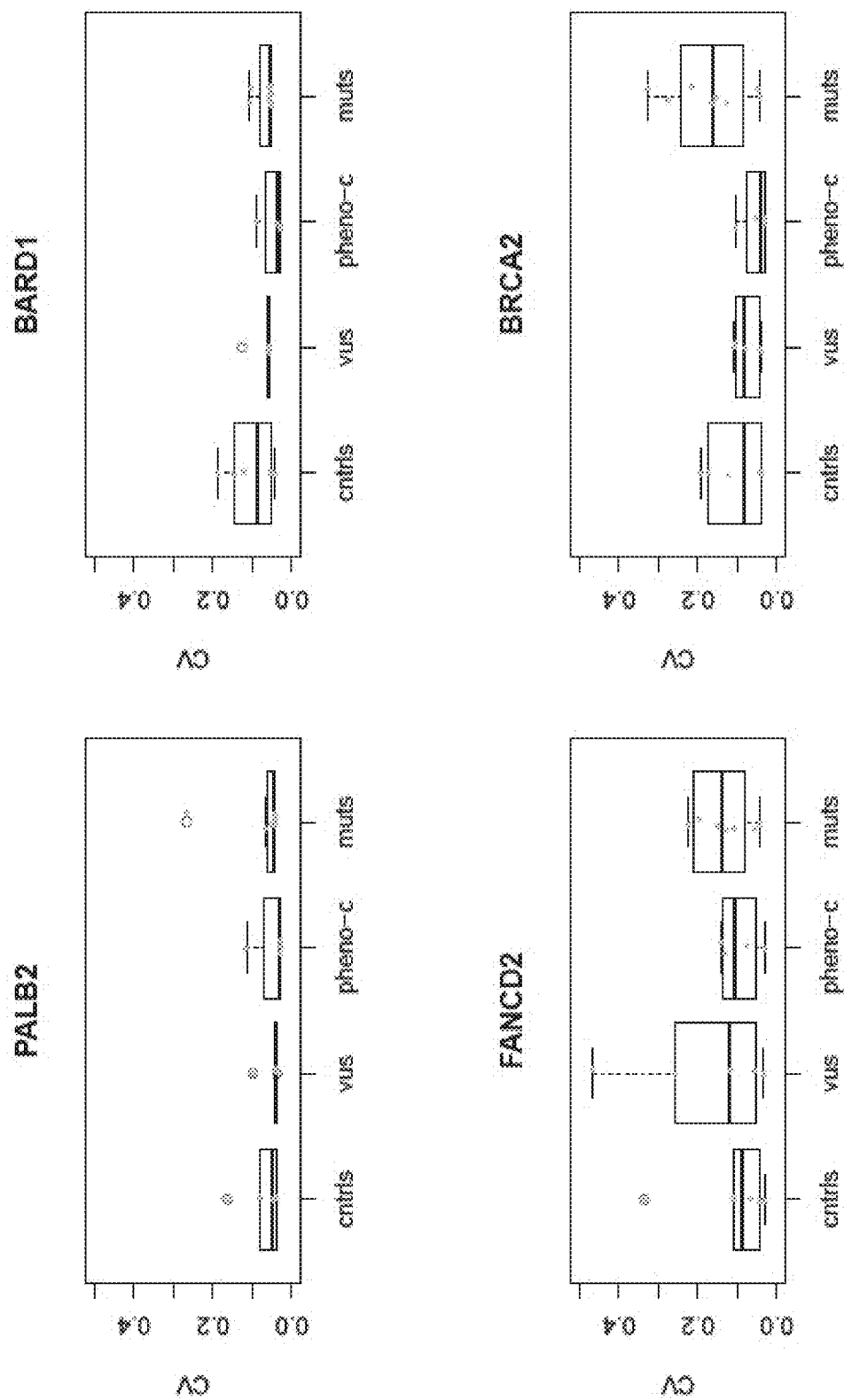
FIG. 7. Binding assays of BRCA1 to interacting proteins have small coefficients of variation (CVs). Boxplots of CVs of individual BRCA1 protein binding assays.
Figure 8:
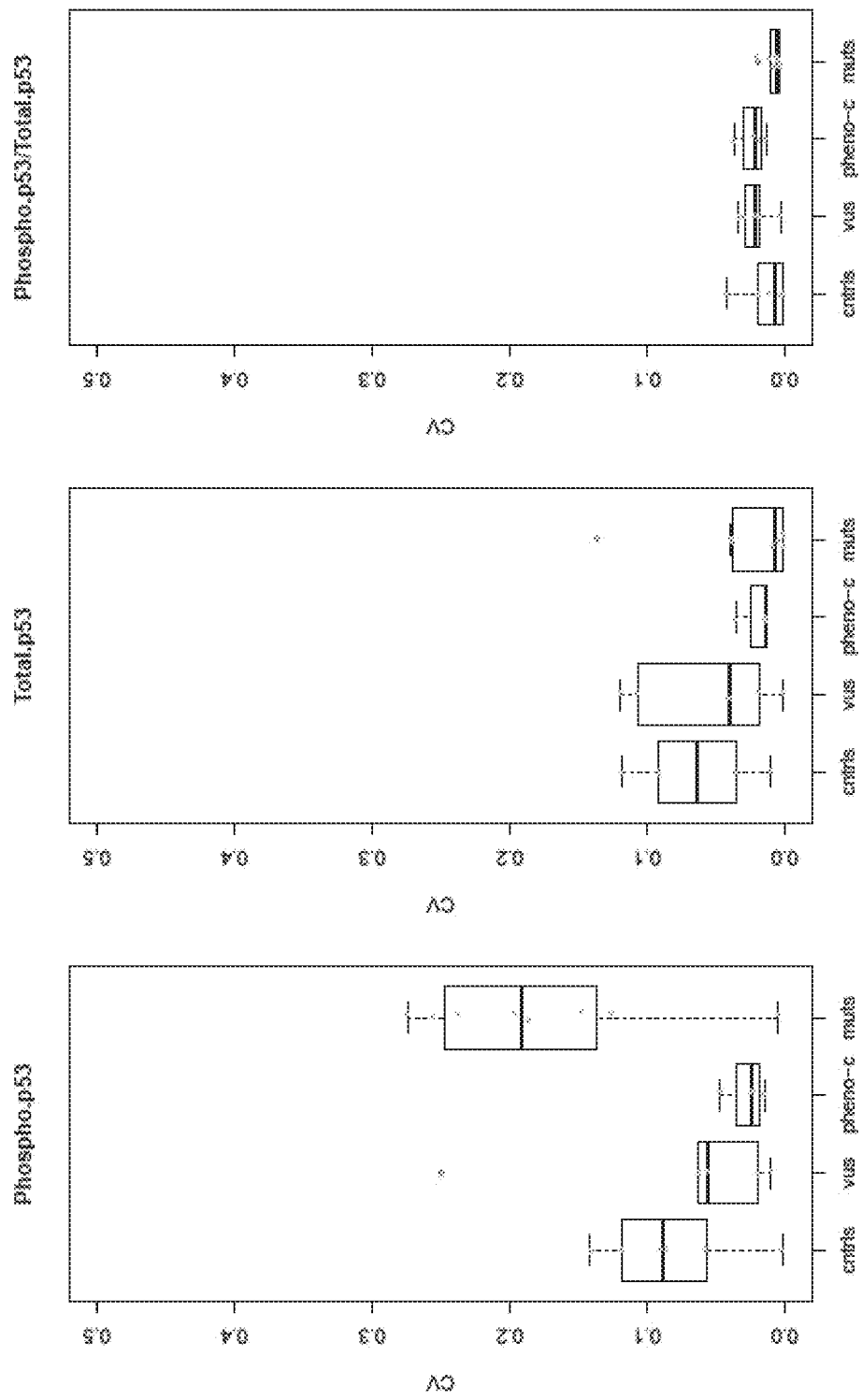
FIG. 8. p53 phosphorylation assays have small coefficients of variation (CVs). Boxplots of CVs of individual p53 phosphorylation assays.

Three sets of BRCA1 variants were assessed in these experiments, known pathogenic mutations, benign variants, and VUS (FIG. 1, see Table 1). The mutations were either stopgain (p.Glu1250Ter, p.Arg1443Ter, p.Tyr1563Ter) (JARA et al., Biol Res, 37:469-481 (2004); CASTILLA et al., Nat Genet, 8: 387-391 (1994); SEROVA et al., Am J Hum Genet, 58:42-51 (1996)), indel (c.66_67 delAG) (STRUEWING et al., Nat Genet, 11: 198-200 (1995)), or single nucleotide variants in the RING (p.Cys61Gly) (GORSKI et al., Am J Hum Genet, 66:1963-1968 (2000)), DNA binding (p.Ser1040Asn) (FRIEDMAN et al., Nat Genet, 8:399-404 (1994)), coiled-coil (p.Arg1443Gly) (CASTILLA et al., Nat Genet, 8: 387-391 (1994)), or BCRT (p.Val1713Ala) domains (Table 1) (STRUEWING et al., Am J Hum Genet, 57:1-7 (1995); CARVALHO et al., Cancer Res, 67:1494-1501 (2007)). The variants with measurable frequencies of homozygotes for the minor allele (p.Asp693Asn, p.Ser784Leu, p.Pro871Leu, p.Glu1038Gly, p.Lys1183Arg, p.Ser1613Gly) were classified as benign and the remainders (p.Gln356Arg, p.Arg841Trp, p.Tyr856His, p.Glu1250Lys) were classified as VUS. For the cell lines from the 1000 Genomes Project with the benign variants or VUS, review of the genomic sequences demonstrated that one cell line, NA20412, had two VUS (p.Arg841Trp and p.S993N). The remainder of the cell lines did not have pathogenic mutations in known breast cancer genes (see Table 1). Thus, with one possible exception, the cell lines with the benign variants truly represented controls. The assays reported here were shown to have small coefficients of variation (CVs) among the 9 replications, indicating the quantitative and reproducible nature of each (FIG. 6-8). Pairwise comparison between the CVs of controls and CVs of mutants, and phenocopies and VUS was made using the exact version of the Mann-Whitney test and yielded non-significant p-values among all comparisons.

Mutations in BRCA1 Alter Nuclear Localization of BRCA1 in Response to Radiomimetic Agents—

Figure 2:
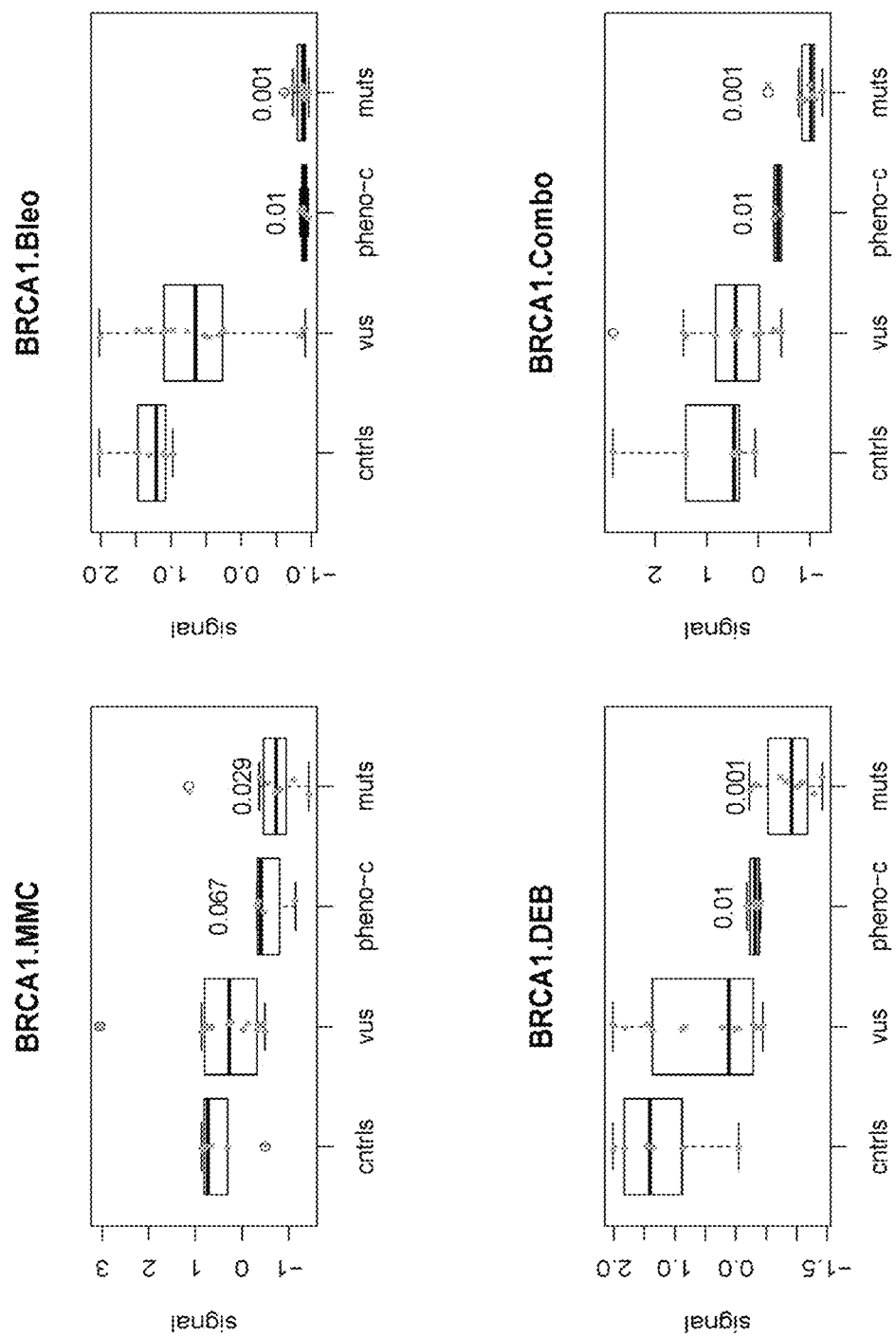
FIG. 2. Cell culture in the presence of radiomimetic agents reduces nuclear localization in BRCA1 mutation-bearing and phenocopy cell lines. Boxplots comparing the standardized localization of BRCA1 in response to Mitomycin C (MMC), Bleomycin (Bleo), Diepoxybutane (DEB) or combination (Combo) treatment for control (cntrls), variants of uncertain significance (VUS), phenocopy (Pheno-C) or mutant (muts) LCLs. P-values of the pairwise comparisons of the various distributions of treatment groups relative to cntrls by the Mann-Whitney test are shown.
Figure 9:
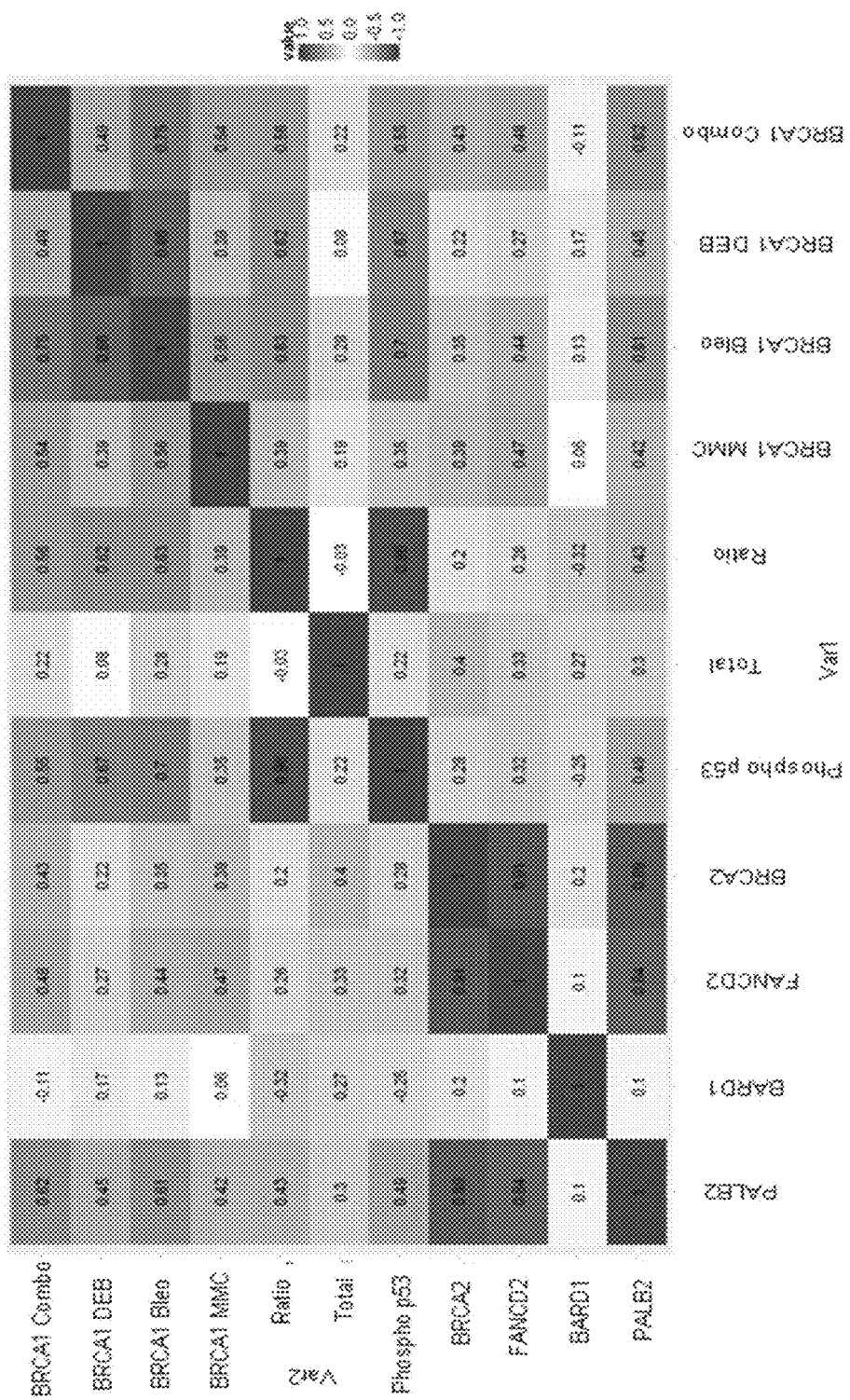
FIG. 9. Correlation plot of each individual FVA against all other FVAs. Comparison between assays present in matrix where 1 is highest (Phosphop53 with BRCA1 MMC and BRCA1 DEB with BRCA1 Combo) and 0.1 is lowest (BARD1 with FANCD2).

BRCA1, BRCA2, PALB2, BARD1, FANCD2 and other members of this protein complex co-localize and form nuclear foci during S phase of the cell cycle (SCULLY et al., Cell, 88:265-275 (1997); CHEN et al., Mol Cell, 2:317-328 (1998)). From their location along the synaptonemal complex in meiotic cells they play a role in recombination and genomic integrity. The process of forming nuclear foci is triggered by agents that promote DNA damage (VENKIT-ARAMAN, Annu Rev Pathol, 4:461-487 (2009)). To test the effect of such radiomimetic DNA damaging agents on BRCA1 nuclear localization, synchronized LCLs were treated with the DNA crosslinking drugs, MMC and DEB, and the DNA breakage drug, Bleo, both individually and in combination of the three, then total and nuclear BRCA1 were measured. The standardized (mean centered, standard deviation scaled per assay) amount of nuclear BRCA1 in LCLs with BRCA1 mutations was reduced compared to controls, both for the individual DEB (Mann-Whitney test p=0.001), MMC (p=0.029), Bleo (p=0.001), or drug combination treatments (p=0.001) (FIG. 2). Thus, these nuclear localization assays can readily discriminate known mutations from wild type controls. The BRCA1 nuclear localization assays showed strong correlation with each other; the strongest correlations were observed for the DEB and Bleo treatments (FIG. 9).

Mutations in BRCA1 Alter Binding to Co-Factors PALB2, BRCA2, and FANCD2.

Figure 3:
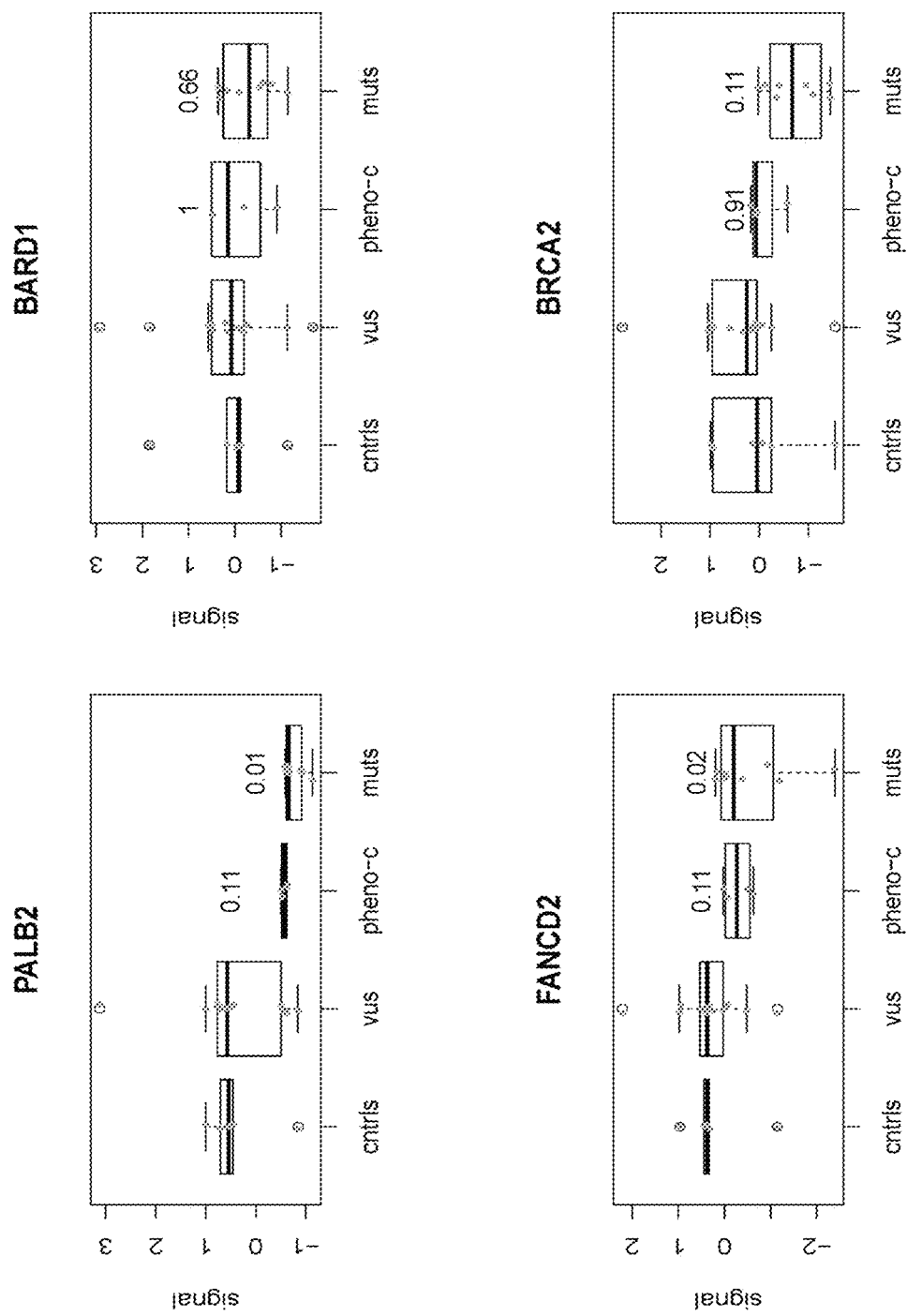
FIG. 3. Binding of BRCA1 to interacting proteins is reduced in BRCA1 mutation-bearing and phenocopy cell lines. Boxplots comparing the standardized binding of PALB2, BARD1, FANCD2 and BRCA2 to BRCA1 in control (cntrls), variants of uncertain significance (VUS), phenocopy (Pheno-C) or mutant (muts) LCLs. P-values of the pairwise comparisons of the various distributions of treatment groups relative to cntrls by the Mann-Whitney test are shown.

Mutations in BRCA1 affect binding to cofactors—either by modifying the site at which the binding takes place, by modifying the folding of the BRCA1 protein and the protein binding sites, or by modifying the quantity of BRCA1 within the cells. BARD1 binds to the RING domain and PALB2 binds to the coiled-coiled domain. Other factors do not bind directly to BRCA1, but rather to the binding partners of BRCA1 forming a protein binding complex (FIG. 1). As observed in the protein co-immunoprecipitation assay, the binding of BRCA1 was markedly reduced to PALB2 (Mann-Whitney p=0.01) and FANCD2 (p=0.02), but not to BARD1 and BRCA2 in the mutant LCLs compared to control LCLs (FIG. 3). Thus, two of these binding assays discriminated high-risk mutations from benign variants. The binding of these proteins to BRCA1 was the same among the control and VUS cell lines. These PALB2, BRCA2, and FANCD2 binding assays showed strong correlation with each other, reflecting the known interaction of these factors with each other and their shared role in initiating homologous recombination (see FIG. 9) (D'ANDREA, *N Engl J Med,* 362: 1909-1919 (2010)).

Mutations in BRCA1 Decrease Phosphorylation of p53.

Figure 4:
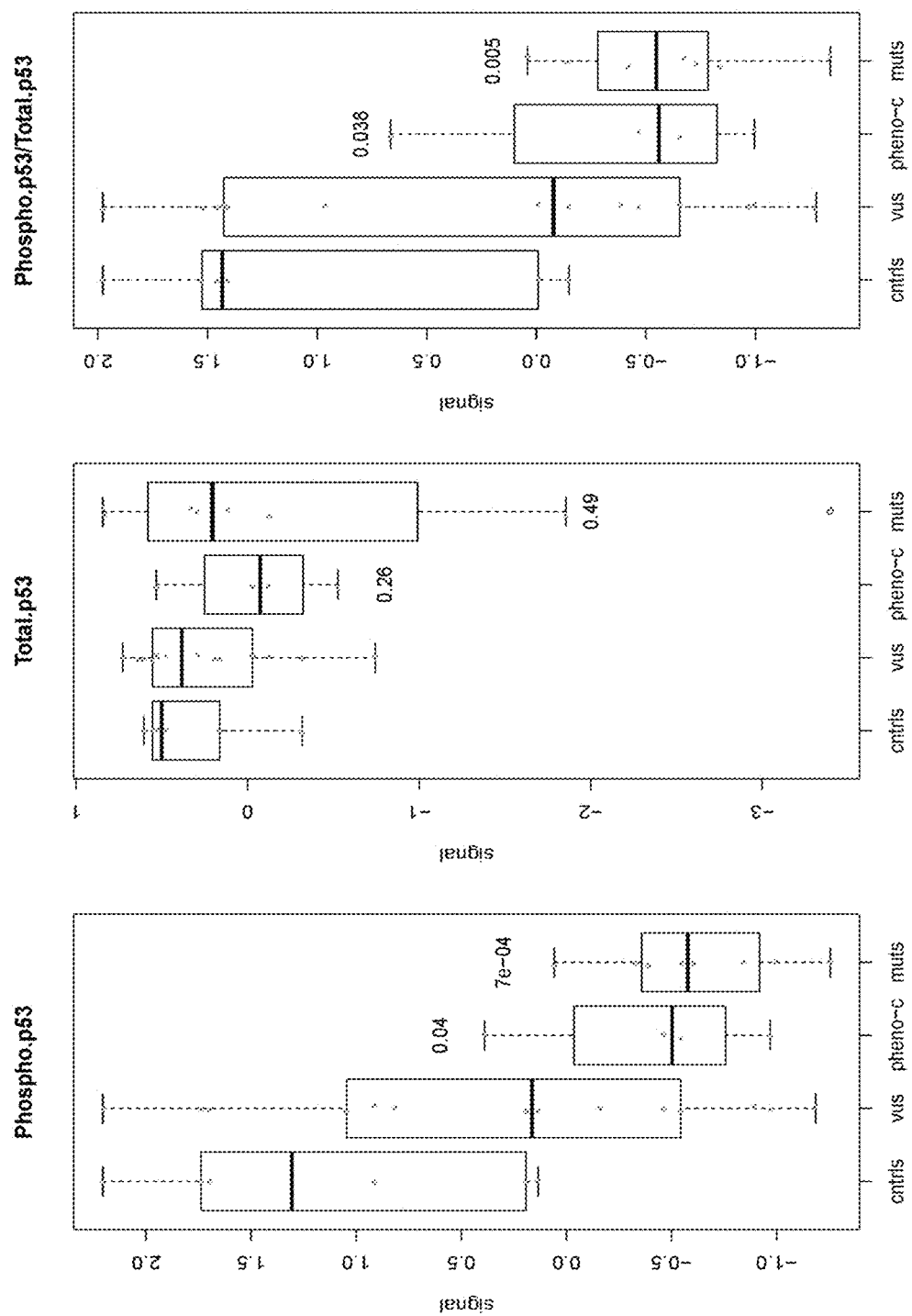
FIG. 4. Phosphorylation of p53 is reduced in BRCA1 mutation-bearing and phenocopy cell lines. Boxplots comparing standardized phospho-p53, total p53 and phospho-p53/total p53 ratio measured by DCW-NUCLEAR LOCALIZATION in control (cntrls), variants of uncertain significance (VUS), phenocopy (Pheno-C) or mutant (muts) LCLs. P-values of the pairwise comparisons of the various distributions of treatment groups relative to cntrls by the Mann-Whitney test are shown.

One of the functions of BRCA1 is to phosphorylate p53, an activity that may be altered by mutations in the BRCA1 gene. For each of the cell lines, both total p53 and phospho-p53 were measured by the digital cell Western technique. Total p53 was the same among the control, BRCA1 mutant and VUS LCLs (FIG. 4). Phospho-p53 and phospho-p53/total p53 ratio were reduced in the mutant LCLs compared to control LCLs (Mann-Whitney p=0.007, p=0.005, respectively); thus, measuring phospho-p53 may enhance the accuracy of identifying mutations. Phospho-p53 and phospho-p53/total p53 ratio were strongly correlated with each other and were also correlated with the nuclear localization assays, especially following treatment with DEB, Bleo or combo (see FIG. 9).

A Cluster of BRCA1 Mutations that Includes BRCA2, FANCD2, FANCC, ATM and NBN Phenocopies.

Figure 5:
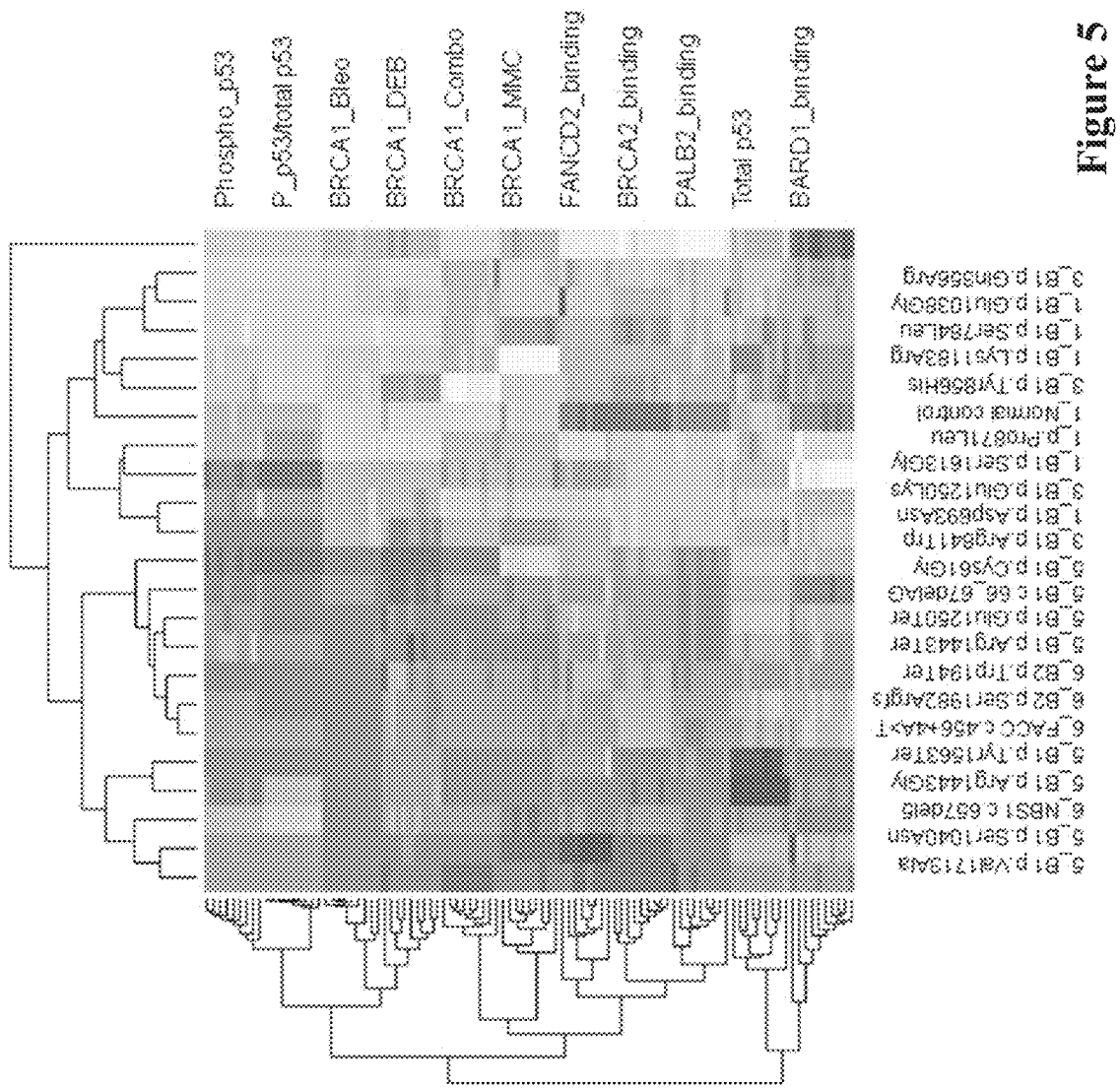
FIG. 5. BRCA1 mutation-bearing and phenocopy cell lines form a distinctive cluster. Heatmap of protein binding, p53 phosphorylation, and nuclear localization assays demonstrates two clusters—mutants and phenocopies (left) and controls (right). The mutants and phenocopies are interdigitated suggesting their similarity and the controls and VUS are interdigitated suggesting their similarity. B1=BRCA1, B2=BRCA2, 1=control, 3=VUS, 5=mutant, 6=phenocopy.

A heatmap of the unsupervised cluster analysis of all of these assays demonstrated two apparent clusters, suggestive of two categories, the mutants, which are interdigitated with each other, and the controls and VUS, which are clustered together (FIG. 5). The overlap of the VUS and controls is consistent with previous reports of >80% of VUS representing benign variants.[6] Pathogenic mutations in BRCA2 (p.Ser1982Argfs, c.983del4, c.6503delTT, p.Tyr42Cys, c.6174delT, c.6426delTT, p.Lys3326Ter, and p.Trp194Ter) as well as single pathogenic mutations in FANCD2 (p.Arg1236His), FANCC (c.456+4A>T), FANCF (p.Gln6Ter), ATM (c.6404insTT, p.Trp2638Ter) and NBN (c.657del5) in LCLs were assessed in all of these assays. These mutant cell lines showed reduction for the DEB (Mann-Whitney p=0.01), Bleo (p=0.01), and combo nuclear localization assays (p=0.01), p53 phosphorylation assay (p=0.04), and phospho-p53/total p53 ratio (p=0.038), suggesting phenocopies for mutations in BRCA1 (FIGS. 2, 4 and 5). The heatmap demonstrated that the BRCA2, FANCC and NBN LCLs were interdigitated with the BRCA1 mutations, supporting the notion that they represent phenocopies. Reductions in the binding of PALB2, BRCA2, and FANCD2 to BRCA1 were not observed for these mutant LCLs. These results suggest that the nuclear localization assay may serve as a basis for identifying pathogenic mutations in the DSB repair pathway, whereas the binding assays can be used to distinguish mutations in the BRCA1 from mutations in other genes.

Discussion

FVAs using modified flow cytometry with fluorescently labeled antibodies were developed to address the need for high throughput, quantitative immunoassays that assess the phenotypic effects of genetic variants on protein quantification, post-translational modification and interactions with other proteins. The selection of these assays assesses the role of BRCA1 and its binding partners in controlling the assembly and activity of macromolecular complexes that monitor DSBs and DNA crosslinks, a role that has been previously termed, "chromosomal custodian (VENKITARAMAN, *Science* 343:1470-1475 (2014))."

The FVAs comprise two principal methods. In DCW-NUCLEAR LOCALIZATION, fluorescent probes are annealed at room temperature to permeabilized fixed cells rapidly and assessed with modified flow cytometry to quantify proteins and their post-translational modifications. Based on individual signal intensity, each cell is measured independently for its protein expression level. For each experiment, 100,000 to a million data points are normalized and calculated as a digital value, hence Digital Cell Western. Here, the technique was modified to include not only measurement of total and phospho p53, but also measurement of BRCA1 in intact cells or the nuclear fraction. In turn, the nuclear localization of BRCA1 was augmented by exposing the cells to the radiomimetic drugs, MMC, DEB and Bleo. In the protein co-immunoprecipitation assay, a specific protein complex is bound to an antibody-coupled bead matrix, and then quantified for interactions with various binding partners. In the case of BRCA1, the bound proteins included PALB2, FANCD2, BRCA2 and BARD1. These FVAs are rapid, quantitative, low-cost and modular for multiple analytes. Thus, they can be readily adapted to the clinical laboratory unlike the previously described transcription activation, small colony phenotype, rescue of radiation resistance, ubiquitin ligase activity, or cisplatin or PARB inhibitor sensitivity complementation assays that require transfection, use of non-host cells and extended periods of culture (CARVALHO et al., *Int J Biochem Cell Biol,* 39: 298-310 (2007); BOUWMAN et al., *Cancer Discov,* 3:1142-1155 (2013)). For example, the cisplatin or PARB inhibitor sensitivity complementation assays in mouse ES cells takes 8 weeks from start to finish versus the 2 days for the FVAs (BOUWMAN et al., *Cancer Discov,* 3:1142-1155 (2013)). The aggregate large number of data points collected for each assay assures that the results are highly quantitative with narrow CVs and thus can measure small differences between different variants or treatment conditions. The assays can assess any variant in the BRCA1 gene and are not confined to the BRCT domain as were the previously described proteolysis, phosphopeptide binding, and transcriptional activation assays (LEE et al., *Cancer Res,* 70:4880-4890 (2010)).

When FVAs were applied to BRCA1 variants, three different classes were observed—full loss-of-function mutations whose molecular effects exceeded a threshold and produced a physical phenotype of reduced localization, reduced binding and reduced phosphorylation, partial loss-of-function or hypomorphic alleles whose molecular effects were reduced for some assays, but not others, and did not produce a recognized physical phenotype (observed as blocks of red or dark orange in the heatmap (FIG. 5), and normal variants, whose activities were constant for the various assays over the multiple controls. Hypomorphic alleles have been observed previously for some BRCA1 variants, such as p.Arg1699Gln in the BRCT domain of BRCA1 that abrogates the repression of microRNA-155 and is associated with a 2-fold increase in cancer risk (CHANG et al., *Nat Med,* 17:1275-1282 (2011)) Most of the FVAs correlated with each other. The pairwise correlation analysis suggests that one nuclear localization assay in response to a radiomimetic agent and the phospho p53 assay would suffice for capturing the range of phenotypic effects in this data set. When clustered, these assays blunted the hypomorphic effects of some alleles and resulted in two overall allelic classes—mutations and benign variants. As noted, this finding is in keeping with the observation that most VUS have been reclassified over time as benign variants, as additional data have accumulated (MURRAY et al., *Genet Med,* 13:998-1005 (2011)). These observations are compatible with the previous suggestion that gene heterozygosity suffices for cancer predisposition, and may trigger a low, but quantitatively significant, level of genome instability that accumulates over many cell divisions (VENKITARAMAN, *Science* 343:1470-1475 (2014)).

In mutants examined, mutations in other DSB repair genes produced phenocopies of the mutations in BRCA1. Reflecting the shared mechanisms, BRCA2 and FANCD2 bind to the BRCA1 complex, whereas NBN co-localizes with this complex at the site of the DSB. These observations suggest that this suite of FVAs may assess not only risks of VUS in BRCA1, but of any VUS in genes in the DSB pathway. Clearly to achieve clinical utility, the assays will have to be adjusted to circulating B cells (or other circulating cells that express these proteins) and tested over a wider range of variants to understand their accuracy. To achieve clinical utility and validity, the assays can be adjusted to circulating B cells (or other circulating cells that express these proteins). As noted, only 2 assays may be required. These assays could serve as an adjunct to sequencing when a VUS has been identified or could also stand alone without sequencing for assessing breast and ovarian cancer risks.

Materials and Methods

Cell Lines and Mutations.

Lymphoblastoid cell lines (LCLs) from subjects with sequence-identified variants in BRCA1 (GM14097 p.Cys61Gly, GM14090 c.66_67 delAG, GM20412 p.Arg841Trp, GM13711 p.Ser1040Asn, GM13713 p.Glu1250Ter, GM14637 p.Arg1443Ter, GM13710 p.Arg1443Gly, GM13708 p.Tyr1563Ter, GM14092 p.Val1713Ala), BRCA2 (GM14805 p.Trp194Ter, GM14170 p.Ser1982Argfs, GM14622 c.6503delTT, GM14623 p.Tyr42Cys, GM14624 p.Ser1982Argfs, GM14626 p.Lys3326Ter, GM14639 c.6426delTT, GM14788 c.983del4), FANCC (GM20731 c.456+4A>T), FANCD2 (GM16756 p.Arg1236His), FANCF (GM16757 p.Gln6Ter), ATM (GM01525 c.6404insTT, GM03332 p.Trp2638Ter (Son), GM03334 p.Trp2638Ter (Parent)) and NBN (GM15788 c.657_661 del5) were purchased from the Coriell Institute Human Genetic Cell Repository (Camden, N.J.). LCLs with other sequence identified variants in the BRCA1 gene from the 1000 Genomes Project (GM12873 p.Gln356Arg, HG00099 p.Asp693Asn, GM 19740 p.Ser784Leu, GM18628 p.Tyr856His, GM11995 p.Pro871Arg, GM10850 p.Glu1038Gly, GM07056 p.Lys1183Arg, GM19084 p.Glu1250Lys, GM11894 p.Ser1613Glywere also purchased from the Coriell Institute. The variants were classified as pathogenic mutations, benign variants or variants of uncertain significance (VUS) (Table 1). Pathogenic variants were either truncating stopgain or indel, or SNVs with consistent reports of pathogenicity across databases and studies. Variants with observed homozygotes in the BRCA1 gene for the minor allele were classified as benign, because homozygosity for deleterious mutations has been reported to be embryonic lethal (HAKEM et al., *Cell*, 85:1009-1023 (1996); GOWEN et al., *Nat Genet*, 12:191-194 (1996)). Variants with discordant reports were classified as VUS.

The sequences of the cell lines derived from the 1000 Genomes Project were analyzed for mutations in other genes reported as moderately to highly penetrant for breast cancer when mutated (AXIN2, BARD1, BMPR1A, BRCA1, BRCA2, FANCD2, GEN1, MLH1, PALB2, POLD1, POLE, PMS2, RAD51C, RAD51D, TP53, XRCC2). The variant annotation was performed by literature review as well as reports in ClinVar at the NCBI web site of the National Institutes of Health, and the Breast Cancer Information Core Database also provided by the National Institutes of Health.

EBV immortalized B-lymphoblastoid cell lines were maintained in RPMI 1640 and DMEM supplemented with 10% and 15% fetal bovine serum, respectively, and cultured in $CO_2$ jacketed 37° C. incubators according to the manufacturer's recommendations (GIBCO, Life Technologies, Grand Island, N.Y., USA). The cells were starved for 24 hours for cell synchronization prior to all experiments. This study was approved by the institutional review board of the Albert Einstein College of Medicine.

Antibodies and Functional Variant Analysis.

Antibodies were obtained for native or phosphorylated forms of proteins. For protein co-immunoprecipitation assays, the following antibodies were used: BRCA1 (Origene TA 310042), BRCA2 (Origene TA313520), PALB2 (Origene TA306814), BARD1 (Origene TA313499), FANCD2 (Origene TA307630), Total p53 (BD 554294), and Phospho-p53 (BD 560282). The BRCA1 antibody was covalently coupled to magnetic beads and the efficiency of binding was determined to be above 90% (data not shown). All of the antibodies were conjugated with fluorochromes (Innova Bio lightning-link APC: 326-0010, FITC: 322-0010, PECy7:762-0010, APCCy7:765-0010, PECy5.5: 761-0010 and RPE:703-0010).

Functional Variant Analyses (FVAs).

The general approach for the analyses included cell culture+/−use of radiomimetic agents. The cell culture was followed by cell fixation and permealization with binding of labeled antibodies within cells or cell lysis with binding of BRCA1 protein complexes to beads and subsequent antibody binding to interacting proteins. For a typical experiment, 2 million isolated LCLs were cultured in suspension in each well of a 6-well plate in RPMI medium (Invitrogen A2780), supplemented with 15% (v/v) FBS Defined Grade, 50 units/ml penicillin, and 50 g/ml streptomycin at 37° C. with 5% $CO_2$. Three biological replicates and three technical replicates each were performed. The previously described methods (LOKE et al., *Clin Genet*, 81:272-277 (2012); LOKE et al., *Hum Mol Genet*, 23:1073-1083 (2014)) were modified as follows:

For the BRCA1 nuclear localization assays, the cultured cells were serum starved for 24 hours prior to treatment either by the vehicle or the radiomimetic drugs: 0.1 µg/ml Bleomycin, 0.5 µg/ml 1,3-butadiene diepoxide (DEB), and/or 1.5 µg/ml Mitomycin C (MMC) or combination for 24 hours. For nuclear extraction of cells, 200,000 cells cultured in 96-well plate were washed with PBS, then lysed using Cytolysis Buffer (20 mM Tris-HCl (pH 7.4), 150 mM NaCl, 10 mM MgCl2, 2 mM EDTA, 10% glycerol, 1% NP-40, 1% Triton X-100, 2.5 mM betaglycerophosphate, 1 mM NaF, 1 mM dithiothreitol, and complete protease inhibitors—Roche). This resulted in cytolysis of ~50% of cells. The nuclei and intact cells were collected by centrifugation, then resuspended in Universal FVA Buffer (50 mM Tris-HCl pH 7.4, 100 mM NaCl, 5% FBS, 0.02% Sodium Azide). The whole prep was probed with fluorochrome-conjugated anti-BRCA1 and endoplasmic reticulum antibodies (whole cell discrimination), stained with DAPI and analyzed by BDFAcsRIA II and BD Canto II.

The binding of BRCA1-interacting proteins was measured by the FVA co-immunoprecipitation assays on Dynabeads. Using BRCA1 as bait, the binding of BRCA2, PALB2, BARD1, and FANCD2 were gated and quantified using fluorochromes-conjugated antibodies. The binding were compared for the mutant, VUS and wild type LCLs.

The relative abundance of total and phospho-p53 were measured by the FVA digital cell Western analysis, as described previously to quantify ERK½ and p38 in cells using fluorochrome-conjugated anti-native and anti-phosphorylated protein antibodies (LOKE et al., *Clin Genet*, 81:272-277 (2012); LOKE et al., *Hum Mol Genet*, 23:1073-1083 (2014)). The quantified total p53, phospho-p53, and phospho-p53/total p53 ratio were compared for the mutant, VUS and wild type LCLs.

Quantitative Analysis.

Flow cytometry was performed using BD FACSAria II and BD Canto II equipped with Blue (488 nm), Green (532 nm), Yellow (561 nm), Red (638 nm) and Violet lasers (407 nm). Briefly, Side-scatter height (SSC-H) was plotted against Side-scatter width (SSC-W) to exclude doublets and to identify fixed intact cells and nuclei. Each target signal was normalized to total gated population of the single cell/bead measurements. All experiments were standardized with single color controls made using fluorophore labeled target antibodies conjugated to Dynabeads using the methods described (19). To make results comparable across assays and cell types, the intensity signals were log transformed and standardized (mean centered, standard deviation scaled) on an assay basis. Unsupervised hierarchical cluster analysis was performed for all technical replicates from individual assays and presented as a dendrogram and heatmap. The mean of nine technical replicates was calculated for each individual cell line assay, and box plots and Mann-Whitney tests were performed to determine whether the differences in nuclear localization, protein binding and p53 phosphorylation were significant between cell lines from wild type and other subgroups (phenocopies and mutants). The dependences among assays was assessed and presented using a Pearson correlation matrix (see FIG. 6). Using all 11 assays, K-means clustering with k=2 was used to classify the cohort of samples (i.e. cell lines) into k=2 subgroups (wild-type versus mutant). K-means clustering (k=2) was also conducted using each pair of assays and each of the 11 assays alone. The clustering results of each individual and paired assay were compared with the clustering of all 11 assays and reported as the phi coefficients (equivalent to the absolute values of Pearson's correlation coefficients) in Table 2.

TABLE 1

| Coriell Catalog ID | Mutation | dbSNP ID | Call | 1000 Genomes Project Phase 1 all populations Genotype Count | Reference (PMID) |
|---|---|---|---|---|---|
| NIGMS Human Genetic Cell Repository | | | | | |
| GM01525 | ATM p.Lys2073fsX2135 | rs16857 | 5 | | |
| GM03332 | ATM p.Trp2638Ter | rs10640 | 5 | | |
| GM14097 | BRCA1 p.Cys61Gly | rs28897672 | 5 | | 10788334, SCRP |
| GM14090 | BRCA1 c.66_67delAG | rs80357713 | 5 | | 7550349 |
| GM20412 | BRCA1 p.Arg841Trp | rs1800709 | 3 | 3 (A\|G) 1089 (G\|G) | 8968716 |
| GM13711 | BRCA1 p.Ser1040Asn | rs4986852 | 5 | 26 (C\|T) 1066 (C\|C) | 7894493 |
| GM13713 | BRCA1 p.Glu1250Ter | rs28897686 | 5 | | 15515971 |
| GM14637 | BRCA1 p.Arg1443Ter | rs41293455 | 5 | | OMIM, SCRP |
| GM13710 | BRCA1 p.Arg1443Gly | rs41293455 | 5 | | SCRP, 7894491 |
| GM13708 | BRCA1 p.Tyr1563Ter | rs80357433 | 5 | | SCRP, 8554067 |
| GM14092 | BRCA1 p.Val1713Ala | rs80357132 | 5 | | 7611277, 17308087 |
| GM14170 | BRCA2 p.Ser1982Argfs | rs80359550 | 5 | | 8673092 |
| GM14805 | BRCA2 p.Trp194Ter | rs80358809 | 5 | | 8673091 |
| GM14622 | BRCA2 c.6503delTT | rs12132 | 5 | | |
| GM14623 | BRCA2 p.Tyr42Cys | rs12133 | 5 | | |
| GM14626 | BRCA2 p.Lys3326Ter | rs12135 | 5 | | |
| GM14639 | BRCA2 c.6426delTT | rs12143 | 5 | | |
| GM14788 | BRCA2 c.983del4 | rs12191 | 5 | | |
| GM16756 | FANCD2 p.Arg1236His | rs16112 | 5 | | |
| GM16757 | FANCF p.Gln6Ter | rs18809 | 5 | | |
| GM20731 | FACC c.456 + 4A > T | rs104886456 | 5 | | 8348157 |
| GM15788 | NBS1 c.657_661del5 | rs21371 | 5 | | 9590180 |
| 1000Genomes Project | | | | | |
| GM12873 | BRCA1 p.Gln356Arg | rs1799950 | 3 | 61 (C\|T) 1031 (T\|T) | 11400546 |
| HG00099 | BRCA1 p.Asp693Asn | rs4986850 | 1 | 6 (T\|T) 75 (C\|T) 1011 (C\|C) | 22703879 |
| GM19740 | BRCA1 p.Ser784Leu | rs55914168 | 1 | 1 (A\|G) 1091 (G\|G) | SCRP |
| GM18628 | BRCA1 p.Tyr856His | rs80356892 | 3 | 8 (A\|G) 1084 (A\|A) | 9510469 |
| GM11995 | BRCA1 p.Pro871Leu | rs799917 | 1 | 313 (A\|A) 429 (A\|G) 350 (G\|G) | SCRP, 22703879 |
| GM10850 | BRCA1 p.Glu1038Gly | rs16941 | 1 | 124 (C\|C) 414 (C\|T) 554 (T\|T) | 22703879 |
| GM07056 | BRCA1 p.Lys1183Arg | rs16942 | 1 | 130 (C\|C) 448 (C\|T) 514 (T\|T) | 16026807 |
| GM19084 | BRCA1 p.Glu1250Lys | rs28897686 | 3 | | 15515971 |
| GM11894 | BRCA1 p.Ser1613Gly | rs1799966 | 1 | 133 (C\|C) 449 (C\|T) 510 (T\|T) | 22703879, 15689452 |

TABLE 2

Correlation of paired and single assays against 11 assays

| Assay_1 | Assay_2 | r | Assay | r |
|---|---|---|---|---|
| Phospho.p53 | BRCA1.MMC | 1 | BRCA1.Bleo | 0.84 |
| BRCA1.DEB | BRCA1.Combo | 1 | BRCA1.MMC | 0.82 |
| FANCD2 | Phospho.p53 | 0.91 | BRCA1.Combo | 0.82 |
| BRCA2 | Phospho.p53 | 0.91 | Phospho.p53 | 0.74 |
| Phospho.p53 | BRCA1.Bleo | 0.91 | BRCA1.DEB | 0.74 |
| Phospho.p53 | BRCA1.DEB | 0.91 | PALB2 | 0.73 |
| Phospho.p53 | BRCA1.Combo | 0.91 | Ratio | 0.63 |
| Ratio | BRCA1.Bleo | 0.91 | FANCD2 | 0.34 |
| BRCA1.MMC | BRCA1.DEB | 0.91 | BRCA2 | 0.34 |
| BRCA1.Bleo | BRCA1.DEB | 0.91 | Total | 0.25 |
| PALB2 | BRCA1.Bleo | 0.84 | BARD1 | 0.16 |
| PALB2 | BRCA1.DEB | 0.84 | | |
| PALB2 | BRCA1.Combo | 0.84 | | |
| FANCD2 | BRCA1.Bleo | 0.84 | | |
| FANCD2 | BRCA1.Combo | 0.84 | | |
| BRCA2 | BRCA1.Bleo | 0.84 | | |
| BRCA2 | BRCA1.Combo | 0.84 | | |
| Total | BRCA1.Bleo | 0.84 | | |
| Total | BRCA1.Combo | 0.84 | | |
| BRCA1.MMC | BRCA1.Bleo | 0.84 | | |
| BRCA1.Bleo | BRCA1.Combo | 0.84 | | |
| PALB2 | Phospho.p53 | 0.82 | | |
| FANCD2 | BRCA1.DEB | 0.82 | | |
| Total | BRCA1.MMC | 0.82 | | |
| Ratio | BRCA1.DEB | 0.82 | | |
| Ratio | BRCA1.Combo | 0.82 | | |
| BRCA1.MMC | BRCA1.Combo | 0.82 | | |
| PALB2 | Ratio | 0.74 | | |
| FANCD2 | Ratio | 0.74 | | |
| BRCA2 | Ratio | 0.74 | | |
| Total | BRCA1.DEB | 0.74 | | |
| Ratio | BRCA1.MMC | 0.74 | | |
| PALB2 | BARD1 | 0.73 | | |
| PALB2 | FANCD2 | 0.73 | | |
| PALB2 | BRCA2 | 0.73 | | |
| PALB2 | Total | 0.73 | | |
| BARD1 | BRCA1.Bleo | 0.73 | | |
| BARD1 | BRCA1.Combo | 0.73 | | |
| BARD1 | BRCA1.MMC | 0.72 | | |
| PALB2 | BRCA1.MMC | 0.66 | | |
| BARD1 | Ratio | 0.63 | | |
| BARD1 | BRCA1.DEB | 0.63 | | |
| FANCD2 | BRCA1.MMC | 0.63 | | |
| BRCA2 | BRCA1.DEB | 0.63 | | |
| Phospho.p53 | Ratio | 0.63 | | |
| BRCA2 | BRCA1.MMC | 0.55 | | |
| FANCD2 | BRCA2 | 0.54 | | |
| Total | Ratio | 0.54 | | |
| BARD1 | BRCA2 | 0.4 | | |
| FANCD2 | Total | 0.34 | | |
| BRCA2 | Total | 0.34 | | |
| Phospho.p53 | Total | 0.25 | | |
| BARD1 | Phospho.p53 | 0.21 | | |
| BARD1 | Total | 0.13 | | |
| BARD1 | FANCD2 | 0.1 | | |

What is claimed is:

1. A method comprising:
   obtaining circulating white blood cells from a subject; treating the white blood cells with a DNA damaging agent; performing a flow cytometry based functional variant analysis (FVA);
   measuring in the treated cells BRCA2 nuclear localization; comparing a measured functional activity with at least one control value obtained from control white blood cells treated with the DNA damaging agent and having a wild type BRCA2 gene; and categorizing variants of the BRCA2 gene in the subject as functional, having loss of function or having a gain of function, based on the comparing step.

2. The method of claim 1, wherein said at least one control value is measured from normal white blood cells or white blood cells having a normal DNA DSB repair pathway.

3. The method of claim 1, wherein said at least one control value is measured from white blood cells with a defective DNA DSB pathway and cancer risks.

4. The method of claim 1, wherein said at least one control value is established at an earlier time.

5. The method of claim 1, wherein said at least one control value is established in parallel to the measurement of the functional activity of the DSB repair pathway in the white blood cells from said subject.

6. The method of claim 1, wherein said white blood cells are selected from the group consisting of B cells, lymphoblastoid cells and total white blood cells.

7. The method of claim 1, where the white blood cells are cultured prior to treatment with a DNA damaging agent.

8. The method of claim 1, wherein the DNA damaging agent is selected from radiation, a chemical compound, or a combination thereof.

9. The method of claim 8, wherein said radiation is UV, x-ray or gamma-ray.

10. The method of claim 9, wherein said compound is selected from the group consisting of Mitomycin C (MMC), 1,3-butadiene diepoxide (DEB), Bleomycin(Bleo), or a combination thereof.

11. The method of claim 1, wherein BRCA2 nuclear localization is measured in an assay using one DNA damaging agent.

12. The method of claim 1, wherein BRCA2 nuclear localization is measured in multiple assays each using a different DNA damaging agent.

13. The method of claim 1, wherein BRCA2 nuclear localization is measured using a DCW (digital cell Western) nuclear localization assay format.

14. The method of 1, wherein the at least one functional activity is measured by a flow cytometer.

15. The method of 1, wherein the white blood cell is a cultured cell.

16. The method of claim 13, wherein the DCW nuclear localization assay comprises
   fixing the treated cells,
   subjecting the treated cells to cell lysis conditions that causes lysis of a predetermined percentage of cells,
   collecting the nuclei and unlysed cells by centrifugation,
   resuspending the collected nuclei and unlysed cells in a staining buffer comprising an optically active agent-conjugated anti-BRCA2 antibody and an optically active agent-conjugated antibody specific for a protein localized intracellularly and outside of the nucleus,
   measuring the amount of BRCA2 protein localized to the nuclei and the total amount of BRCA2 protein in the cells, and
   determining the ratio of the amount of BRCA2 protein localized to the nuclei versus the total amount of BRCA2 protein expressed in the cells as basis of determining said functional activity of BRCA2.

* * * * *